United States Patent [19]

Murray

[11] Patent Number: 4,981,973
[45] Date of Patent: Jan. 1, 1991

[54] TRANSVINYLATION REACTION
[75] Inventor: Rex E. Murray, Charleston, W. Va.
[73] Assignee: Union Carbide Chemicals and Plastics Company, Inc., Danbury, Conn.
[21] Appl. No.: 213,697
[22] Filed: Jun. 30, 1988
[51] Int. Cl.$^5$ .................. C07C 41/05; C07C 67/02
[52] U.S. Cl. .................. 548/229; 560/176; 560/217; 585/639; 585/640
[58] Field of Search .............. 585/639, 640; 560/176, 560/217; 548/229

[56] References Cited

U.S. PATENT DOCUMENTS

| Re. 27,663 | 6/1973 | Fernholtz et al. | 260/497 A |
|---|---|---|---|
| 827,718 | 2/1960 | Mayne et al. | |
| 877,103 | 9/1961 | Mayne et al. | |
| 2,245,131 | 0/0000 | Herrmann et al. | 260/476 |
| 2,299,862 | 10/1942 | Toussaint et al. | 260/410 |
| 2,989,554 | 6/1961 | Mayne et al. | 260/410.9 |
| 2,997,494 | 8/1961 | Brown | 260/410.9 |
| 3,000,918 | 9/1961 | Wilip et al. | 260/410.9 |
| 3,117,145 | 1/1964 | Ehrreich | 260/410.9 |
| 3,158,633 | 11/1964 | Port et al. | 260/410.9 |
| 3,179,641 | 4/1965 | Brown et al. | 260/87.1 |
| 3,188,319 | 6/1965 | Smidt et al. | 260/326 |
| 3,201,357 | 8/1965 | Fang | 560/217 |
| 3,337,611 | 8/1967 | Beardon, Jr. | 260/491 |
| 3,391,130 | 7/1968 | Bolstad et al. | 260/89.1 |
| 3,454,644 | 7/1969 | Dewhirst | 260/570.9 |
| 3,560,534 | 2/1971 | MacDonald | 260/410.9 |
| 3,647,832 | 3/1972 | Chabardes et al. | 260/429 J |
| 3,725,305 | 4/1973 | Wilkinson | 252/429 R |
| 3,751,449 | 8/1973 | Gobran et al. | 260/486 R |
| 3,755,387 | 8/1973 | Young | 260/410.9 N |
| 3,786,102 | 1/1974 | Godfrey | 260/615 R |
| 3,793,355 | 2/1974 | Wilkinson | 260/429 R |
| 3,965,155 | 6/1976 | Smith et al. | 260/491 |
| 3,965,156 | 6/1976 | Smith et al. | 260/491 |
| 4,112,235 | 9/1978 | Schmerling | 560/1 |
| 4,175,056 | 11/1979 | Antos | 252/441 |
| 4,415,499 | 11/1983 | Blum et al. | 260/410.9 N |
| 4,424,359 | 1/1984 | Kaschig | 546/255 |
| 4,446,073 | 5/1984 | Qualeatti et al. | 260/409 |
| 4,458,088 | 7/1984 | Hardman | 560/217 |
| 4,640,802 | 2/1987 | Drent | 260/410.9 R |
| 4,647,691 | 3/1987 | Lin | 560/175 |
| 4,658,053 | 4/1987 | Green | 560/234 |
| 4,664,851 | 5/1987 | Drent | 560/175 |
| 4,731,467 | 3/1988 | Drent et al. | 560/204 |

FOREIGN PATENT DOCUMENTS 1249847  9/1967  Fed. Rep. of Germany ...... 560/175

OTHER PUBLICATIONS

Sandler, S. R., Journal of Chemical and Engineering Data, vol. 14, No. 4, Oct. 1966, pp. 503-506.
Slinckx, G. and Smets, G., Tetrahedron, vol. 22, 1966, pp. 3163-3171.
Hopff, H. and Osman, Maged A., Tetrahedron, vol. 24, 1968, pp. 3887-3890.
Adelman, R. L. Journal Organic Chemistry, 14, 1949, pp. 1057-1077.
Henry, P. M., Accounts of Chemical Research, vol. 6, 1973, pp. 16-24.
Sabel, A. et al., Chem. Ber. 102, 1969, pp. 2939-2950.
McKeon, J. E. et al. Tetrahedron, vol. 28, 1972, pp. 227-232.
McKeon, J. E. et al., Tetrahedron, vol. 28, 1972, pp. 233-238.
Secemski, I. I. et al., Journal of the American Chemical Society, vol. 93, No. 14, 1971, pp. 3547-3550.
Henry, P. M., Journal of the American Chemical Society, vol. 93, No. 16 1971, pp. 3853-3859.
Henry, P. M., Journal of the American Chemical Society, vol. 94, No. 21, 1972, pp. 7311-7315.
Henry, P. M., Journal of the American Chemical Society, vol. 94, No. 21, 1972, pp. 7316-7322.
Pandey, R. N. et al., Canadian Journal of Chemistry, vol. 53, 1975, pp. 2223-2231.
Allen, N. P. et al., Inorganica Chimica Acta, 28, 1978, pp. 231-235.
Rotem, M. et al., Organometallics, 2, 1983, pp. 1689-1691.
Mitsudo, T. et al., J. Org. Chem., vol. 50, No. 9, 1985, pp. 1566-1568.
Mitsudo, T. et al., J. Org. Chem., vol. 52, No. 11, 1987, pp. 2230-2239.
Vinyl Polymers (Acetate), Kirk-Othmer Encyclopedia of Chemical Technology, Third Edition, vol. 23, pp. 817-847.
Crooks, G. R. et al. J. Chem. Soc. (A), 1969, pp. 2761-2766.
Cotton, F. A. et al., Chemical Communications, 1971, pp. 967-968.
Spencer, A. et al., J. C. S. Dalton, 1972, pp. 1570-1577.
Legzdins, P. et al., J. Chem. Soc. (A), 1970, pp. 3322-3326.
Gareev, G. A. et al., Zhurnal Organicheskoi Khimii, vol. 13, No. 3, 1977, pp. 606-607.
Robinson, S. D. et al., J. C. S. Dalton, 1973, pp. 1912-1920.
Fouda, S. A. et al., Inorganic Chemistry, vol. 17, No. 11, 1978, pp. 3213-3220.
Spencer, A., Inorg. Nucl. Chem. Letters, vol. 12, 1976, pp. 661-663.
Komiya, S. et al., Chemistry Letters, 1987, pp. 1287-1290.
Leonard, Edward C., Vinyl and Diene Monomers, Part 1, Higher Polymers, vol. XXIV, Wiley Interscience, pp. 331-334.

Primary Examiner—Robert A. Wax
Assistant Examiner—Frederick F. Tsung
Attorney, Agent, or Firm—Gerald L. Coon

[57] ABSTRACT

A process for the transvinylation of a vinyl derivative of a Bronsted acid with a different Bronsted acid which comprises providing a liquid phase mixture containing said vinyl derivative and said Bronsted acid in the presence of a ruthenium compound at a temperature at which transvinylation occurs and recovering as a product of transvinylation the vinyl derivative of the different Bronsted acid. The process is most favorably employed using carboxylic acids to make vinyl esters of carboxylic acids.

78 Claims, No Drawings

TRANSVINYLATION REACTION

BRIEF DESCRIPTION OF THE INVENTION

There is described a process for the transvinylation of a vinyl derivative of a Bronsted acid with a different Bronsted acid which comprises providing a liquid phase mixture containing said vinyl derivative and said Bronsted acid in the presence of a ruthenium compound at a temperature at which transvinylation occurs and recovering as a product of transvinylation the vinyl derivative of the different Bronsted acid.

BACKGROUND TO THE INVENTION

Transvinylation or vinyl interchange technology has existed for several decades. The reaction can be illustrated by the reaction of a vinyl ester or vinyl ether with an active hydrogen containing compound, as in the following:

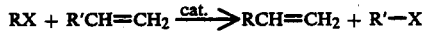

$$RX + R'CH=CH_2 \xrightarrow{cat.} RCH=CH_2 + R'-X$$

wherein R is carboxy, amido, aroxy, alkoxy, and the like; X is hydrogen, hydroxyl, alkyl, aryl, and the like; and R' is carboxyl, amido, alkyl, substituted alkyl, aryl or substituted aryl.

Adelman, *Journal Organic Chemistry*, 14, pp. 1057–1077, 1949, at p. 1057, termed transvinylation "the 'Vinyl Interchange' Reaction, to differentiate it from typical ester interchange and ester-acid interchange reactions" . . . Adelman noted the following advantages for this reaction:

"The very mild reaction conditions and the low yields of by-products lead to high yields of monomers of greater purity and activity than those prepared by the reaction of acetylene with acids."
"Furthermore, vinyl esters of dibasic acids are prepared much more easily by vinyl interchange than through the acetylene route, and recent work in this laboratory has shown that the reaction of vinyl acetate catalyzed with mercuric salts is not restricted to carboxylic acids, but will occur with other compounds containing active hydrogen, such as acetoacetic ester and glycolic esters."

McKeon, et al., *Tetrahedron*, 28, pp. 227–232 (1972) show the vinyl interchange reaction between a vinyl ether and an alcohol using a palladium catalyst. Other sources report the transvinylation reaction between vinyl chloride and a carboxylic acid.

The literature suggests that the preferred catalysts for transvinylation reactions have been mercury and palladium based compounds. However, Pt (II) and Rh (III) have been reported by A. Sabel, J. Smidt, R. Jira and H. Prigge, *Chem. Ber.*, 102, pp. 2939–2950 (1969), to catalyze the reaction. In addition, Young, U.S. Pat. No. 3,755,387, patented Aug. 26, 1973, entitled: "A Vapor Phase Transvinylation Process", claims the use of supported Hg, Pd, Pt, Ir, Rh, Ru, or Os salt catalysts in a vapor phase transvinylation process. The experimental portion discloses the use of only palladium on carbon, copper on carbon, iron on carbon, palladium/copper on carbon, palladium/copper/iron on silica, mercuric acetate on carbon, and mercuric chloride on carbon. Hg and Pd are cited, at col. 1, line 67, as the preferred metals. There is no recognition by this patentee of any special advantages to (i) the use of ruthenium compounds as catalysts for transvinylation reactions and (ii) effecting the reaction in a liquid phase reaction using a ruthenium compound as the catalyst.

Significant deficiencies in these prior art technologies are:

1. The mercury-based catalyst is toxic, undesirably volatile, and is typically activated with sulfuric acid to promote reaction and then deactivated by neutralization with base prior to product distillation. Traces of adventitious free acid generated by this system tend to promote ethylidene diester formation.
2. Palladium-based catalysts are not sufficiently thermally stable to allow product removal by distillation at elevated temperatures; the catalyst often deactivates forming metallic Pd.

M. Rotem, et al., *Organometallics*, 2, pp. 1689–1691 (1983), T. Mitsudo, et al., *J. Org. Chem.*, 50, pp. 1566–1568 (1985), and T. Mitsudo, et al., *J. Org. Chem.*, 52, pp. 2230–2239 (1987) show the use of ruthenium based catalysts to promote the addition of carboxylic acids to alkynes and producing alkenyl carboxylates. In particular, the reaction of carboxylic acids with substituted alkynes is facile. The reaction of carboxylic acids with acetylene (vinylation) to give vinyl esters is also possible, but at a much slower rate. Various catalyst precursors have been studied which include ruthenium carbonyl, bis(eta 5-cyclooctadienyl)ruthenium (II)/tri-n-butylphosphine, and bis(eta 5-cyclooctadienyl)ruthenium (II)/trialkylphosphine/maleic anhydride.

The use of these and similar ruthenium compositions as transvinylation catalysts has apparently not been recognized until this invention. The beneficial use of ruthenium-containing compounds as catalysts for transvinylation processes which overcome several of the deficiencies noted for the prior art catalysts has not been appreciated until this invention.

There is a need in the transvinylation art for a catalyst having high catalytic activity at convenient elevated temperatures which would allow the facile removal of the desired product of the reaction without interfering with other components present in the reaction product mixture.

THE INVENTION

The invention relates to a process for the transvinylation of a vinyl derivative of a Bronsted acid with a different Bronsted acid which comprises providing a liquid phase mixture containing said vinyl derivative and said Bronsted acid in the presence of a ruthenium compound at a temperature at which transvinylation occurs and recovering as a product of transvinylation the vinyl derivative of the different Bronsted acid. In the preferred practice of the process, the ruthenium is soluble in the reaction mixture in a catalytically effective amount.

DETAILS OF THE INVENTION

Transvinylations are equilibrium reactions. The efficiency of the reaction is measured by the extent the desired transvinylation reaction product is present in the equilibrium reaction products. In other words, the reaction generates more than one product and the effectiveness of the process is frequently measured by the proportion of the desired product to the other products of the transvinylation reaction.

The reaction of the invention involves the combination of

◊ a vinyl derivative of a Bronsted acid;

◊ a different Bronsted acid with which to interchange;
◊ a ruthenium compound; and
◊ liquid phase reaction conditions.

The vinyl derivative is any compound in which there is a vinyl group bonded to a Bronsted acid. They may be characterized as vinylated Bronsted acids. Vinyl embraces groups of the formula $$R^0R^1C=CH—$$

wherein $R^0$ and $R^1$ are each individually one of hydrogen, alkyl of 1 to about 12 carbon atoms, cycloalkyl, aryl, alkyl ethers, and the like. The Bronsted acid is any species which can act as a source of protons.

Illustrative of suitable vinyl derivatives of a Bronsted acid for the practice of the invention, are vinyl acetate, vinyl pivalate, vinyl benzoate, vinyl methacrylate, vinyl acrylate, divinyl isophthalate, divinyl terephthalate, divinyl adipate, vinyl propionate, vinyl stearate, vinyl salicylate, vinyl cinnamate, vinyl 2-ethylhexanoate, vinyl cyclohexanoate, N-vinyl pyrrolidinone, N-vinylsuccinimide, vinyl phenyl ether, vinyl methyl ether, vinyl ethyl ether, N-vinyl 2-oxazolidinone, N-vinyl ethyleneurea, N-vinyl N-acetylethyleurea, 2-vinyloxyethyl acetate, 2-vinyloxyethyl pivalate, 2-vinyloxyethylacrylate, vinyl chloride, vinyl sulfonamides, and the like.

Preferred vinyl derivatives are the vinyl esters of carboxylic acids and the vinyl alkyl or aryl ethers, mainly because they are more commercially available.

Illustrative of suitable Bronsted acids for the practice of the invention are carboxylic acids such as monocarboxylic and polycarboxylic acids illustrated by acetic acid, propionic acid, butyric acid, pivalic acid and other neo acids, stearic acid, and other vinyl esters of fatty acids, benzoic acid, terephthalic acid, isophthalic acid, phthalic acid, adipic acid, succinic acid, malic acid, maleic acid, polyacrylic acids, crotonic acid, acrylic acid, methacrylic acid, salicylic acid, cinnamic acid, 2-ethylhexanoic, and cyclohexanoic acid; amides such as 2-pyrrolidinone, 2-pyrrolidone, ε-caprolactam, 2-oxazolidinone, ethyleneurea, N-acetyl ethyleurea, and succinimide; alcohols such as methanol, ethanol, n-propanol, isobutanol, fluorinated alkanols such as 1,1,1,3,3,3-hexafluoro-2-propanol, monoethanolamine, diethanolamine, and triethanolamine; phenolic compounds such as phenol, resorcinol, and Bisphenol A [2,2-bis(4-hydroxyphenyl)propane]; amino compounds which are sufficiently acidic such as secondary aromatic amines, azoles, blocked amines and imines, silazanes, and the like; hydroxy esters such as hydroxalkyl acrylates (viz., 2-hydroxethyl acrylate, 2-hydroxyethyl methacrylate) and hydroxyalkyl alkanoates (viz., 2-hydroxyethyl acetate, 2-hydroxyethyl pivalate); sulfonamides such as diethyl sulfonamide and toluene sulfonamide; silanols such as phenyl silane triol, diphenyl silane diol, triphenyl silane mono-ol, dimethyl silane diol, trimethylsilane mono-ol, and the like.

The preferred Bronsted acids are the carboxylic acids, the alcohols, the imines, the amides, the imides, the phenolics, and the like.

Illustrative of transvinylation reactions that may be carried out by the process of the invention, are the following:

| Vinyl Derivative | Bronsted Acid | Product |
|---|---|---|
| vinyl acetate | + pivalic acid | → vinyl pivalate |
| vinyl benzoate | + pivalic acid | → vinyl pivalate |
| vinyl acetate | + methacrylic acid | → vinyl methacrylate |
| vinyl acetate | + acrylic acid | → vinyl acrylate |
| vinyl acetate | + isophthalic acid | → divinyl isophthalate |
| vinyl acetate | + terephthalic acid | → divinyl terephthalate |
| vinyl propionate | + adipic acid | → divinyl adipate |
| vinyl acetate | + benzoic acid | → vinyl benzoate |
| vinyl acetate | + propionic acid | → vinyl propionate |
| vinyl pivalate | + stearic acid | → vinyl stearate |
| vinyl acetate | + salicyclic acid | → vinyl salicylate |
| vinyl acetate | + cinnamic acid | → vinyl cinnamate |
| vinyl propionate | + 2-ethylhexanoic acid | → vinyl 2-ethylhexanoate |
| vinyl acetate | + cyclohexanoic acid | → vinyl cyclohexanoate |
| vinyl acetate | + 2-pyrrolidinone | → N-vinyl 2-pyrrolidinone |
| vinyl pivalate | + 2-pyrrolidinone | → N-vinyl 2-pyrrolidinone |
| vinyl pivalate | + succinimide | → N-vinyl succinimide |
| vinyl methyl ether | + phenol | → vinyl phenyl ether |
| vinyl chloride | + methanol | → vinyl methyl ether |
| vinyl methyl ether | + ethanol | → vinyl ethyl ether |
| vinyl acetate | + 2-oxazolidinone | → N-vinyl 2-oxazolidinone |
| vinyl acetate | + ethyleneurea | → N-vinyl ethyleneurea |
| vinyl acetate | + N-acetyl ethyleneurea | → N-vinyl N-acetylethyleurea |
| vinyl acetate | + 2-hydroxyethyl acetate | → 2-vinyloxyethyl acetate |
| vinyl pivalate | + 2-hydroxyethyl pivalate | → 2-vinyloxyethyl pivalate |
| vinyl pivalate | + 2-hydroxyethylacrylate | → 2-vinyloxyethyl acrylate |

The process of this invention provides an excellent route to many hard to produce vinyl compounds because of the desirable physical and chemical properties of the ruthenium compounds which provide the basis for the catalytic reaction. The ruthenium catalysts are easily obtainable as soluble components and can be used in the form of non-volatile compounds possessing high thermal stability, and exhibiting high catalytic activity only at elevated temperatures. Unlike palladium, the ruthenium-based catalyst does not lead to observable metal precipitation, even when reaction is conducted at temperatures above 150° C. From a practical standpoint, the physical and chemical properties of the ruthenium catalyst (soluble, non-volatile, and possessing high thermal stability) permit product removal by distillation. These properties suggest that the ruthenium catalyst system is far superior to prior art transvinylation technologies using palladium and mercury.

The selection of a suitable ruthenium compound to provide the catalytic activity for the transvinylation reaction is not narrowly critical. Essentially any ruthenium compound can be effectively employed to carry out the transvinylation reaction. However, the invention is believed to involve novel ruthenium-based catalysts which to promote the vinyl interchange (transvinylation) between vinyl derivatives and the Bronsted acids. It is believed the primary requirement for the generation of such catalysts and the requisite catalytic activity are ruthenium precursors to the catalyst which can be converted to [Ru(CO)$_2$RCO$_2$] or similar compounds even if the precursor during the reaction fails to be converted to such structures. [Ru(CO)$_2$RCO$_2$] or similar compounds may or may not be the transvinylation catalyst of the invention but it has been noted that the use of such compounds assures the effective catalytic reaction and the results herein characterized. The process of this invention may be practiced with a vast array of ruthenium compounds. Even instances where the ruthenium compound is too stable for catalyzing the reaction, catalysts can be effected by including a compound which does not adversely affect the transvinylation reaction and stimulates the ruthenium compound to be converted to a species having catalytic activity. For example, ruthenium chloride is a sluggish catalyst but is made quite active by the addition of an alkali such as an alkali metal salt of a carboxylic acid, viz. sodium acetate. It is not presumed that simple ruthenium salt compounds are the catalyst or that many of the ruthenium compounds herein used to effect the catalytic reaction are the catalyst. The exact ruthenium containing compound or compounds that constitute the catalyst of this invention is not appreciated but what is appreciated is that many ruthenium compounds can be used to in situ generate the catalyst. The diversity of the selection of ruthenium compounds suitably employable as precursors to catalysts in the process of the invention is quite broad; illustrative of this point - the precursor compounds may range from supported ruthenium such as ruthenium on carbon, alumina, and the like, to ruthenium carbonyl to bis(eta 5-cyclooctadienyl)ruthenium-(II)/tri-n-butylphosphine and to bis(eta 5-cyclooctadienyl)ruthenium(II)/trialkyl- phosphine/maleic anhydride.

The most preferred catalysts are formed from ruthenium carbonyl carboxylates, or precursors which can convert into these species. Based on an analysis of the literature, certain assumptions of the likely structure of the catalyst have been made. Based on the recognition that ruthenium carbonyl reacts with carboxylic acids to produce soluble orange-yellow complexes possessing the empirical formula [Ru(CO)$_2$RCO$_2$]$_n$ and the fact these complexes appear sufficiently labile to accommodate coordination of vinyl acetate and subsequently catalyze exchanges between vinyl-bound and ruthenium-bound carboxylates, it is believed that such structures are involved in the catalysis of the transvinylation process. For example, it is known that in the presence of carbon monoxide, [Ru(CO)$_2$RCO$_2$]$_n$ is readily converted to Ru$_2$(CO)$_6$(RCO$_2$)$_2$ dimer. Analogously, substitution with other ligands such as phosphines gives Ru$_2$(CO)$_4$(L)$_2$(RCO$_2$)$_2$ complexes. Similar affinity for coordination is thus proposed for vinyl esters. The addition of one equivalent of triphenylphosphine (per ruthenium) to a ruthenium carbonyl-based catalyst reduced transvinylation rate by a factor of about ten, indicating the presumably formed complex, Ru$_2$(CO)$_4$(L)$_2$(-RCO$_2$)$_2$, is a less active precursor. Similarly, the addition of one equivalent of the phosphonium ylide, 2-(triphenylphosphor-anylidene) succinic anhydride, resulted in reduced reaction rates. The complex, hydrido(acetato)tris(triphenyl-phosphine)ruthenium(II), exhibited meager activity, indicating that higher phosphorus to ruthenium ratios lead to a more serious rate inhibition. Tetrahydridotetraruthenium dodecacarbonyl, H$_4$Ru$_4$(CO)$_{12}$, can also be used to form the catalyst. Ruthenium(III) chloride, ruthenium(III) iodide, tris(2,2-bipyridyl)ruthenium(II) chloride hexahydrate, and ruthenocene exhibited only very slight catalytic activity, which further substantiates that the level of catalyst activity intimately depends upon the form of the ruthenium precursor.

It has been found that the presumed catalyst precursor, [Ru(CO)$_2$RCO$_2$]$_n$, can be generated in several ways. For example, the trinuclear complex, [Ru$_3$O-(OAc)$_6$(H$_2$O)$_3$]OAc, gives an efficient transvinylation catalyst. Infrared analysis indicates that [Ru$_3$O(OAc)$_6$(-H$_2$O)$_3$]OAc can convert to [Ru(CO)$_2$RCO$_2$]$_n$ under transvinylation reaction conditions. This is even observed when the reaction is conducted under nitrogen atmosphere, rather than carbon monoxide. Frequently, there is sufficient adventitious carbon monoxide available to in situ convert all of the Ru to a carbonyl form.

As was previously stated, ruthenium trihalide-based precursors, e.g., ruthenium(III) chloride and ruthenium(III) iodide, exhibit only slight activity. However, a very active and more selective catalyst can be generated in situ from ruthenium chloride and sodium acetate. This presumably produces the [Ru$_3$O(OAc)$_6$(-H$_2$O)$_3$]OAc precursor and insoluble sodium chloride salt. The conditions useful for effective catalyst generation includes a ruthenium carboxylate precursor or a mixture of reagents which can generate a ruthenium carboxylate precursor. Dichlorotricarbonylruthenium-(II) dimer, [RuCl$_2$(CO)$_3$]$_2$, also gives an active, but non-selective catalyst which produces significant quantities of heavier by-products, tentatively believed to be ethylidine-and glycol-diesters. It is postulated that upon conversion to catalyst, [RuCl$_2$(CO)$_3$]$_2$ also forms traces of hydrochloric acid which are principally responsible for the by-product formation. There is some very good evidence to substantiate these assumptions. Under similar reaction conditions, but in the absence of ruthenium, hydrochloric acid has been shown to readily promote heavy by-product formation. The salient conclusion is that ruthenium halide precursors can be used in the invention, however they are best used in conjunction with alkali metal carboxylates (typically sodium acetate) to facilitate precipitation of the alkali metal halide (typically sodium chloride). Non-carbonyl and non-carboxylate containing ruthenium compounds can also lead to highly active catalysts. In experiments conducted under carbon monoxide atmosphere, ruthenium-(III) acetyl-acetonate, ruthenium(IV) oxide, ruthenium on carbon, and ruthenium on alumina have all shown catalytic activity. Under these conditions, ruthenium powder shows trace activity. A route to transvinylation catalysts from ruthenium halides involves, as pointed above, displacing the halide from the ruthenium precursor. It is also likely that other metal salts, known to precipitate halides (Ag$^+$, Cu$^+$, Hg$^+$) would also be effective in combination with ruthenium halides to provide the catalyst precursor.

The amount of the ruthenium catalyst useful for effecting the transvinylation reaction is not narrowly critical. The typical amount is a catalytically effective amount, that is, an amount which is sufficient to effect the desired vinyl interchange. For example, it has been established that ruthenium catalyst concentrations ranging roughly from about 30,000 parts to about 0.5 part per million (ppm) ruthenium based on the weight of the liquid phase reaction medium can be used to effect the reaction. It is believed that larger and smaller amounts of the catalyst may be used to effect the reaction. The most preferred range is from about 0.1 ppm to about 500 ppm ruthenium, same basis.

It is desirable that the transvinylation reaction be carried out in the absence of an amount of water in the reaction mixture that inhibits the production of the desired vinyl interchanged product. However, as shown in the Examples 60-63 below, the reaction can be carried out in the presence of significant quantities of water. The inhibiting effects of water are reactant dependent. Increasing the concentration of ruthenium catalyst in the reaction mixture is a facile method of overcoming water inhibition in many cases, if not most cases. It has been noted that there is a correlation between the amount of ruthenium catalyst employed and the amount of water usuable in the process. The more ruthenium present, the more water that may be present in the reaction without adversely affecting the reaction. It is desirable to use a system which is substantially water-free. As a rule, the amount of water present in the reaction is desirably less than about 25 weight % of the weight of the reaction mixture. Preferably, the amount of water in the reaction is less than about 15 weight % of the weight of the mixture. The smaller the amount of water present the better the reaction operates and greater the yield of desired reaction product. Essentially anhydrous reaction systems as herein characterized are preferred. For example, it is more desirable that the amount of water in the reaction be less than about 10 weight % of the weight of the mixture. Preferably, the amount of water in the reaction is less than about 5 weight % of the weight of the mixture, more preferably less than about 2.5 weight % of the weight of the mixture, most preferably less than about 1 weight % of the weight of the mixture. Water concentration in the reaction mixture can be controlled by conventional procedures, such as by drying the reactants carefully, azeotropically distilling the water from the reaction when an azeotrope is formed, and by the addition of molecular sieve drying agent.

The temperature at which the reaction can be carried out is also not narrowly critical. The reaction rate varies with the identity of the Bronsted acid to be transvinylated. The more acidic acids tend to be reactive at lower temperatures. It is also desirable to operate at a temperature at which the acid reactant is dissolved or liquid. The process is favorably effected by keeping the reaction temperature below the boiling point of the highest boiling reactant or at sufficient pressure to maintain the liquid state. When feasible, the liquid phase condition can best be accomplished by operating at temperatures above the melting point of the acid. Nonetheless, terephthalic acid (mp>300° C.), which is insoluble in most catalyst-compatible solvents, was transvinylated to divinyl terephthalate by conducting the reaction in aromatic ester solvents at elevated temperatures (ca. 150° C.). These conditions presumably facilitate transvinylation by achieving slight solubility of the terephthalic acid. Overall, the temperature at which the reactions may be carried out range from about 20° C. to about 300° C., but about 50° C. to about 200° C. is more preferred.

The optimum reaction conditions depend chiefly on the Bronsted acid (such as a carboxylic acid) to be transvinylated. If the acid is soluble at the reaction temperature, it is better to operate without solvent. It is also preferred, when feasible, to conduct the reaction at temperatures above the melting point of the acid.

Transvinylation works best without solvents or in nonpolar solvents. Suitable results have been achieved in solvents such as toluene, heptane, silicone oil, mineral oil, phenylbenzoate, dimethylterephthalate, and dioctylphthalate. More highly polar solvents such as alcohols, water, sulfolane, Carbowaxes®, and N-methylpyrolidinone tend to inhibit reaction rates. Oxygenated aromatics such as diphenylether, methylbenzoate, dimethylterephthalate, and dioctylphthalate are desirable solvents in the synthesis of divinylterephthalate and divinylisophthalate.

The invention is operational over a broad range of mole ratios of Bronsted acid (such as carboxylic acid) to vinyl derivative. The preferred ratios depends mostly on the transformation sought. In general, ratios of about 100/1 to about 1/100 are preferred and ratios of about 1/10 to about 10/1 are most preferred.

The mole ratio of the Bronsted acid (viz., carboxylic acid or carboxylate) to ruthenium should be at least 0.5 to 1. The ruthenium concentration in the reaction mixture is a catalytically effective amount and this is typically in the parts per million range while the acid is typically a major component of the reaction mixture. Most preferably the mole ratio of the Bronsted acid to ruthenium is about 50/1 to about 1,000,000/1.

Several reaction atmospheres, such as carbon monoxide, air, nitrogen, and ethylene, are compatible with the transvinylation catalyst. Nitrogen and ethylene are suitable in most situations. Carbon monoxide appears to improve catalyst selectivity. Air has been employed in conjunction with phenothiazine (polymerization inhibitor) for the synthesis of vinyl acrylates. In some instances the catalytic reaction produces small amounts of methane, carbon monoxide, and carbon dioxide by-products which obviously augment the initially charged reaction atmosphere. The reaction may be carried out at pressures which are subatmospheric, atmospheric or superatmospheric. In some situations, reaction can also be conducted under vacuum such as in a distillation apparatus. A desirable reaction pressure is from about $10^{-6}$ torr to about 5,000 psia. The more desirable reaction pressure is from about $10^{-5}$ torr to about 800 psia. The preferred reaction pressure is from about $10^{-4}$ torr to about 550 psia. The preferred reaction pressure is superatmospheric pressure, typically from about 16 to about 5,000 pounds per square inch absolute.

As pointed out previously the reaction is carried out under conditions at which all of the reactants are in the liquid phase. This does not require that the reaction environment be wholly in the liquid phase. It simply means that sufficient of the reactants and the catalyst be in the liquid phase that the reaction can occur in the liquid phase. For example, solid ruthenium on a solid support can be used as a catalyst precursor. In the presence of reactant, solvent and/or carbon monoxide, sufficient ruthenium can be converted to a liquid soluble compound such that the catalytic reaction is attainable. In another case, reactant can be supplied in a supercritical fluid condition which is sufficiently "liquid" to support the liquid phase conditions of this invention. Much of the reaction system can be in the gas or solid phase, and this would be acceptable so long as enough of the reaction system is in the liquid phase to support the transvinylation reaction of the invention.

A favorable aspect of the process of the invention is to shift the equilibrium of the reaction in the direction of the favored product so that higher concentrations of the product can be obtained based on the amount of starting materials employed. This can be done by the continuous removal of one of the products of the reaction so as to shift the equilibrium in a favorable direction without adversely affecting the catalyst and/or the ruthenium values.

EXAMPLE 1

To a Fischer-Porter bottle were charged ruthenium carbonyl (0.316 grams), benzoic acid (183 grams, 1.50 moles), and vinyl acetate (258 grams, 3.00 moles). The bottle was attached to the reaction apparatus, purged and pressurized to 25 psig with carbon monoxide, and heated to 150° C. for 3 hours. The reaction mixture was cooled to ambient temperature, transferred to a 1 liter flask, and distilled by rotary evaporation under reduced pressure. The fraction taken at approximately 15 torr and 84° C. (187.8 grams) was redistilled through a 15 cm Vigreux column. Vinyl benzoate (100.4 grams, >99% pure by gc) was collected in fractions boiling from 90°–101° C. at 15 torr.

EXAMPLE 2

To a Fischer-Porter bottle were charged tris(aquo)-hexa-$\mu$-aceto-$\mu_3$-oxo-triruthenium acetate (0.032 grams), 2-ethylhexanoic acid (42.37 grams, 0.294 moles), and vinyl acetate (25.3 grams, 0.294 moles). The bottle was attached to the reaction apparatus, purged and pressurized to 25 psig with carbon monoxide, and heated to 150° C. for 3 hours. The reaction mixture was stripped of volatiles by rotary evaporation and the residue was distilled through a 15 cm Vigreux column. A fraction collected at 49° C./5 torr was vinyl 2-ethylhexanoate (9.0 grams, >99% pure by gc).

EXAMPLE 3

To a Fischer-Porter bottle were charged ruthenium carbonyl (0.118 grams), pivalic acid (68.43 grams, 0.67 moles), and vinyl benzoate (48.87 grams, 0.33 moles). The bottle was attached to the reaction apparatus, purged and pressurized to 25 psig with carbon monoxide, and heated to 150° C. for 2 hours. The cooled reaction mixture was charged to a 250 ml flask and vacuum distilled through a 15 cm Vigreux column. A fraction collected at 60.5°–65° C./150 torr (31.7 grams) was redistilled at atmospheric pressure (bp=114° C., 24.2 grams). It comprised vinyl pivalate.

EXAMPLE 4

To a Fischer-Porter bottle were charged ruthenium carbonyl (0.211 grams), adipic acid (7.3 grams, 0.05 moles), and vinyl acetate (21.5 grams, 0.25 moles). The bottle was attached to the reaction apparatus, purged and pressurized to 25 psig with nitrogen, and heated to 130° C. for 4.5 hours. The reaction mixture was stripped of volatiles by rotary evaporation and the residue was distilled through a 15 cm Vigreux column. A fraction collected at 72°–79° C./0.75 torr was divinyl adipate (1.5 grams, >98% pure by gc).

EXAMPLE 5

To a Fischer-Porter bottle were charged tris(aquo)-hexa-$\mu$-aceto-$\mu_3$-oxo-triruthenium acetate (0.9 grams), dioctylphthalate (150 grams), terephthalic acid (75 grams, 0.45 moles), and vinyl acetate (150 grams, 1.74 moles). The bottle was attached to the reaction apparatus, purged and pressurized to 25 psig with carbon monoxide, and heated to 175° C. for 4.5 hours. The reaction mixture was stripped of volatiles by rotary evaporation. Distillation through a short path column afforded a fraction boiling at 111° C./0.7 torr which solidified upon condensing (mp=76.5°–80.5° C.). It contained divinyl terephthalate.

EXAMPLE 6

Using a procedure similar to that of Example 5, isophthalic acid (75 grams) was converted to divinyl isophthalate at successive reaction temperatures of 150° C. for 3.5 hours and 175° C. for 2.25 hours. Distillation through a short path column afforded a fraction boiling at 117°–145° C./1.2 torr (7.1 grams) which solidified upon condensing (mp=53.5°–56.5° C.). It comprised divinyl isophthalate.

EXAMPLES 7–12

The following examples in the following table show a number of ruthenium catalyzed transvinylations conducted between vinyl acetate and a variety of carboxylic acids in which the vinyl ester products, in lieu of isolation, were characterized by either GC/Ir/Mass Spec or by GC retention time compared with an authentic sample. The table lists the reaction conditions.

| Ex. No. | CARBOXYLIC ACID | VINYL ESTER PRODUCT | MAX. TEMP. | REACT. ATMOS. |
|---|---|---|---|---|
| 7 | propionic acid | vinyl propionate | 130° C. | $N_2$ |
| 8 | pivalic acid | vinyl pivalate | 130° C. | $N_2$ |
| 9 | acrylic acid[1] | vinyl acrylate | 100° C. | Air |
| 10 | methacrylic acid[2] | vinyl methacrylate | 100° C. | Air |
| 11 | succinic acid | divinyl succinate | 150° C. | CO |
| 12 | terephthalic acid[3] | divinyl terephthalic | 170° C. | CO |

[1]Phenothiazine was added to the reaction mixture to inhibit polymerization.
[2]Phenothiazine was added to the reaction mixture to inhibit polymerization.
[3]The reaction was conducted in dimethyl terephthalate solvent.

EXAMPLE 13

In three batches which were later combined, ruthenium carbonyl (44.4 grams, total of the three batches), pivalic acid (510 grams, total of the three batches), and vinyl acetate (432 grams, total of the three batches) were charged to Fischer-Porter bottles, flushed and pressurized (25 psig) with carbon monoxide, and heated for approximately 2 hours at 145°–160° C. This procedure resulted in a highly concentrated ruthenium catalyst solution (2.15% ruthenium or 21,500 ppm ruthenium) which as a result of the reaction conditions, was dissolved in an equilibrated mixture of vinyl acetate, pivalic acid, vinyl pivalate, and acetic acid. When charged to the 30 gallon stainless steel reactor as described below with 10 gallons each of vinyl acetate and pivalic acid to make vinyl pivalate, a 300 ppm ruthenium catalyst concentration was achieved.

Vinyl pivalate (91 pounds) was prepared in two, 20 gallon-batch runs in a 30 gallon stainless steel reactor. In two batches, pivalic acid (75.5 lbs, 10 gallons) and vinyl acetate (77.9 lbs, 10 gallons) were transvinylated in the presence of 300 ppm ruthenium catalyst, described in the preceeding paragraph, at 145° C. using a 50 psig carbon monoxide reaction atmosphere for 5 hours. Reaction product was removed from the reactor by vacuum distillation (60°–130° C., 240 mm Hg) from the ruthenium catalyst without difficulty. Based on gas chromatographic analysis, 90.4% and 94.7% of the vinyl pivalate respectively formed in the two reaction batches, could be accounted for after distillation. This demonstrates that reequilibration of vinyl pivalate (and acetic acid) to vinyl acetate (and pivalic acid) was successfully controlled during distillation within 9.6% (batch 1) and 5.3% (batch 2), respectively. Mass balances for all components were better than 98%.

EXAMPLES 14-32

Catalytic activity of numerous ruthenium precursor compounds was evaluated according to the following procedure. A mixture of the ruthenium compound, vinyl acetate (17.2 grams), benzoic acid (12.2 grams) and nonane (internal standard for gas chromatographic analysis) were charged to a Fischer-Porter bottle, sealed, purged three times with carbon monoxide and finally pressurized to 25 psig. The magnetically-stirred reaction mixture was heated in an oil bath to the desired reaction temperature for a specified time period (both specified in the table). Gas chromatagraphic analysis on an DB-1 fused silica capillary column (30M) revealed the amount of vinyl benzoate formed by transvinylation (shown in the table).

| Ex. No. | Catalyst Precursor (grams) | Temp./Time °C./hr | Vinyl Benzoate, grams |
|---|---|---|---|
| 14 | tris(aquo)-hexa-$\mu_3$-oxo-triruthenium heptaacetate (0.211 g) | 102/19[4] | 5.704 |
| 15 | $RuCl_3 \times H_2O$ (0.211 g) | 130/3[5] | 0.287 |
| 16 | $RuCl_3 \times H_2O$ (0.211) sodium acetate (1.0 g) | 130/1 | 4.072 |
| 17 | $Ru_3(CO)_{12}$ (0.211 g) | 130/2[6] | 6.160 |
| 18 | $Ru_3(CO)_{12}$ (0.21 g) | 130/2[7] | 5.025 |
| 19 | $Ru_3(CO)_{12}$ (0.002 g) | 130/2[8] | 1.759 |
| 20 | $Ru_3(CO)_{12}$ (0.021 g) | 130/2[9] | 4.722 |
| 21 | $Ru_3(CO)_{12}$ (0.021 g) | 130/2 | 5.027 |
| 22 | $Ru_3(CO)_{12}$ (0.211 g) triphenylphosphine (0.262 g) | 130/18[10] | 5.723 |
| 23 | ruthenium [5% on carbon], (1.0 g) | 150/4 | 6.067 |
| 24 | ruthenium [5% on alumina], (1.0 g) | 150/18 | 5.421 |
| 25 | ruthenium (III) 2,4-pentanedioate (0.06 g) | 150/4 | 5.957 |
| 26 | ruthenium powder 99.9% (0.06 g) | 150/2 | 0.126 |
| 27 | dichlorotricarbonyl-ruthenium (II) dimer (0.06 g) | 150/2 | 4.277 |
| 28 | ruthenium (IV) oxide, hydrate (0.06 g) | 150/2 | 2.762 |
| 29 | tris(2,2'-bipyridyl) ruthenium (II) chloride, hexahydrate (0.2 g) | 150/2 | NA |
| 30 | ruthenium (IV) oxide, anhydrous (0.06 g) | 150/2 | 0.045 |
| 31 | $H_4Ru_4(CO)_{12}$ (0.06 g) | 150/2 | 7.008 |
| 32 | ruthenium (III) iodide (0.06 g) | 150/2 | 0.029 |

[4] The Fischer-Porter bottle was purged and pressurize with 25 psig nitrogen instead of 25 psig carbon monoxide
[5] See previous footnote
[6] See previous footnote
[7] See previous footnote
[8] See previous footnote
[9] The Fischer-Porter bottle was purged and pressurized with 25 psig ethylene instead of 25 psig carbon monoxide
[10] The Fischer-Porter bottle was purged and pressurize with 25 psig nitrogen instead of 25 psig carbon monoxide

EXAMPLES 33-46

The following table demonstrates transvinylations without product isolation. In the examples recited in the table, ruthenium catalyzed transvinylations (300 ppm ruthenium) of various acidic compounds with either vinyl acetate (VA) or vinyl pivalate (VP) were conducted in a manner in which the vinyl monomer products, in lieu of isolation were characterized by GC/IR/-MASS SPEC or GC retention time compared with an authentic sample. The table lists the reaction conditions.

| Ex. No. | Acidic Compound | Vinyl Source | °C./HR | Product(s) | Verification Technique |
|---|---|---|---|---|---|
| 33 | stearic acid | VA | 150/18 | vinyl stearate | retention |
| 34 | palmitic acid | VA | 150/5 | vinyl palmitate | GC/IR/MS |
| 35 | succinimide | VA | 150/3 | vinyl succinimide | GC/IR/MS |
| 36 | salicylic acid | VA | 160/2 | vinyl salicylate | GC/IR/ MS |
| 37 | phenol | VA | 160/2 | phenyl vinyl ether | GC/IR/MS |
| 38 | 2-pyrrolidinone | VA | 180/0.5 | N-vinyl pyrrolidinone | GC/IR/MS |
| 39 | 2-pyrrolidinone | VP | 160/7[11] | N-vinyl pyrrolidinone | retention |
| 40 | ethylene glycol | VA | 150/2 | 2-methyl 1-3-dioxolane | retention |
| 41 | 2-oxazolidinone | VA | 180/1 | N-vinyl-2-oxazolidinone | GC/IR/MS |
| 42 | ethyleneurea | VA | 180/3 | N-vinyl ethyleneurea | GC/IR/MS |
| 43 | 2-hydroxyethylethyleneurea | VA | 180/3 | 2-hydroxyethyl 5-vinyl ethyl eneurea 1-(2-acetoxyethyl)-2-vinyloxy-imidazoline 2-acetoxyethyl-5-vinyl ethylene urea | GC/IR/MS |
| 44 | 2-hydroxyethyl acetate | VA | 115/2.5 130/2.5 150/2 | 2-vinyloxyethyl acetate | GC/IR/MS |
| 45 | 2-hydroxyethyl pivalate | VP | 150/7 | 2-vinyloxyethyl pivalate | GC/IR/MS |
| 46 | 1,1,1,3,3,3-hexafluoro-2-propanol | VP |  | vinyl (1,1,1,3,3,3-hexafluoro-2-propyl) ether | GC/IR/MS |

[11] 3,000 ppm ruthenium catalyst

EXAMPLES 47-55

Using the procedure for Examples 33-46, the vinyl products recited in Examples 47-55 were made using 300 ppm of ruthenium added as ruthenium carbonyl. Verification was not or has not yet been accomplished, but G-C product peaks are located at logical retention times for these products.

| Ex. No. | Acidic Compound | Vinyl Source | °C./hr. | Product(s) | Verification Technique |
|---|---|---|---|---|---|
| 47 | 2,2-diphenyl acetic acid | VA | 150/6 | vinyl (2,2-diphenyl acetate) | logical retention |
| 48 | 2-benzoyl benzoic acid | VA | 150/3 | vinyl 2-benzoyl benzoate | logical retention |
| 49 | Exxon Neo Acid 913 | VA | 145/3 | vinyl pivalate | logical retention |

| Ex. No. | Acidic Compound | Vinyl Source | °C./hr. | Product(s) | Verification Technique |
|---|---|---|---|---|---|
| | (C—, C—, C— 5 7 9 mixed neo acids) | | | vinyl neo-heptanoate vinyl neo-nonanoate | |
| 50 | 1-hexanol | VP | 150/4 | hexyl vinyl ether | logical retention |
| 51 | 6-amino-caproic acid | VA | 160/4 | vinyl (N-acetyl-amino-caproate) | logical retention |
| 52 | 6-amino-caproic acid | VP | 160/7 | vinyl (N-pivoyl-amino-caproate) | logical retention |
| 53 | tri-n-propyl silanol | VP | | vinyloxy (tri-n-propyl-silane | logical retention |
| 54 | 2-hydroxy-ethyl acrylate | VP | | 2-vinyl-oxyethyl acrylate | logical retention |
| 55 | trimellitic anhydride | VP | | 5-isobenzo-furancarbox-ylic acid, 1,3-di-hydro-1,3-dioxo-ethenyl ester | logical retention |
| 56 | o-toluene-sulfona-mide | VP | | N-vinyl o-toluene sulfona-mide | logical retention |

EXAMPLE 57

To a Fischer-Porter bottle were charged cyclohexanecaboxylic acid (100.0 grams, 0.78 moles), vinyl acetate (134.3 grams, 1.56 moles), and ruthenium cabonyl (0.056 grams). The bottle was sealed, purged four times with carbon monoxide, and pressurized to 25 psig. The bottle was placed in a 150° C. oil bath and stirred for 4.5 hours. The resultant solution after cooling to ambient temperature, was concentrated by rotary evaporation. The residue was distilled through a vigreux column giving a fraction (53.2 grams, 54°-64° C./4/3 mm Hg) which was vinyl cyclohexane carboxylate.

EXAMPLE 58

To a Fischer Porter bottle were charged salicylic acid (13.8 grams, 100 mmoles), vinyl acetate (34.4 grams, 400 mmoles), and ruthenium carbonyl (0.03304 grams). The bottle was sealed, purged four times with carbon monoxide, and pressurized to 25 psig. The bottle was placed in an oil bath and stirred for 2 hours at a 130° C. to 140° C. The resultant solution, after cooling to ambient temperature, was concentrated by rotary evaporation. The residue was distilled through a vigreux column giving a fraction (3.81 grams, 60°-74° C./1.0 mm Hg) which was vinyl salicylate.

EXAMPLE 59

To a Fischer-Porter bottle were charged trans-cinnamic acid (148) grams, 1 mole), vinyl acetate (172 grams, 2 moles), and ruthenium carbonyl (0.201 grams). The bottle was sealed, purged three times with carbon monoxide and pressurized to 25 psig. The bottle was placed in an oil bath and stirred for 3 hours at 145° C. The resultant solution, after cooling to ambient temperature, was concentrated by rotary evaporation. The residue was distilled through a vigreux column giving a fraction (57 grams 112°-130° C./1.0 mm Hg) which was vinyl cinnamate.

EXAMPLE 60

A mixture consisting of propionic acid (12.2 grams), vinyl acetate (17.2 grams), distilled water (0.5011 grams), nonane internal standard (0.864 grams) and ruthenium carbonyl (0.211 grams, a calculated 3,340 ppm Ru concentration) was charged to a Fischer-Porter reaction vessel, purged and pressurized to 25 psig with nitrogen, and heated to 130° C. for 15 hrs. Analysis of the cooled reaction mixture by gas chromatography indicated that the following product composition was present:

| | |
|---|---|
| vinyl acetate | 9.893 grams |
| acetic acid | 5.032 grams |
| vinyl propionate | 7.398 grams |
| propionic acid | 7.488 grams |

EXAMPLE 61

A mixture consisting of propionic acid (12.2 grams), vinyl acetate (17.2 grams,) nonane internal standard (0.8395 grams), and ruthenium carbonyl (0.021 grams, a calculated 334 ppm Ru concentration) was charged to a Fischer-Porter reaction vessel, purged and pressurized to 25 psig with nitrogen, and heated to 150° C. for 2 hrs. Analysis of the reaction mixture by gas chromatography indicated that the following product composition was present.

| | |
|---|---|
| vinyl acetate | 9.759 grams |
| acetic acid | 2.811 grams |
| vinyl propionate | 8.232 grams |
| propionic acid | 5.897 grams |

EXAMPLE 62

The transvinylation of a crude vinyl acetate waste stream from an industial plant which is contaminated with ethyl acetate, vinyl propionate, and approximately 2% water was used to convert the contained vinyl acetate into vinyl propionate. The crude "wet" vinyl acetate (5.0 grams), propionic acid (25.0 grams), nonane standard (0.4225 grams) and ruthenium carbonyl (0.019 grams, 300 ppm Ru) were charged to a Fischer-Porter bottle, purged and pressurized to 25 psig carbon monoxide and heated 3 hrs at 160° C. and sampled. The following products are tabulated:

| | |
|---|---|
| vinyl acetate | 1.227 grams |
| acetic acid | 0.654 grams |
| vinyl propionate | 1.684 grams |

EXAMPLE 63

In this example, the vinyl acetate of Example 62 was azeotropically dried prior to use. The crude vinyl acetate was dried by azeotropic refluxing on a Dean-Stark apparatus for several hours. The "anhydrous" crude vinyl acetate (5.0 grams), propionic acid (25.0 grams), nonane standard (0.4398 grams) and ruthenium carbonyl (0.019 grams, 300 ppm Ru) were charged to a Fischer-Porter bottle, purged and pressurized to 25 psig carbon monoxide and heated 3 hrs at 140° C. and sample. The following products are tabulated

| vinyl acetate | 1.290 grams |
|---|---|
| acetic acid | 0.468 grams |
| vinyl propionate | 3.249 grams |

I claim:

1. A process for the transvinylation of a vinyl derivative of an organic Bronsted acid with a different organic Bronsted acid which comprises providing a liquid phase mixture containing said vinyl derivative and said organic Bronsted acid in the presence of a ruthenium compound selected from the group consisting of ruthenium carbonyl, ruthenium carboxylate, and ruthenium carbonylcarboxylate compounds at a temperature at which transvinylation occurs and recovering as a product of transvinylation the vinyl derivative of the different organic Bronsted acid.

2. A process of claim 1 wherein the ruthenium compound is soluble in the liquid mixture.

3. The process of claim 1 wherein the vinyl derivative is a vinyl ester of a carboxylic acid.

4. The process of claim 3 wherein a product of transvinylation is a vinyl ester of a carboxylic acid.

5. The process of claim 3 wherein the vinyl ester of a carboxylic acid is vinyl acetate.

6. The process of claim 3 wherein the vinyl ester of a carboxylic acid is vinyl pivalate.

7. The process of claim 4 wherein the vinyl ester of a carboxylic acid is vinyl pivalate.

8. The process of claim 3 wherein the vinyl ester of a carboxylic acid is vinyl benzoate.

9. The process of claim 4 wherein the vinyl ester of a carboxylic acid is vinyl benzoate.

10. The process of claim 3 wherein the vinyl ester of a carboxylic acid is a vinyl acrylate.

11. The process of claim 10 wherein the vinyl ester of a carboxylic acid is vinyl acrylate.

12. The process of claim 10 wherein the vinyl ester of a carboxylic acid is vinyl methacrylate.

13. The process of claim 4 wherein the vinyl ester is a vinyl ether of a hydroxyalkyl carboxylate.

14. The process of claim 1 wherein the liquid phase mixture is substantially water-free.

15. The process of claim 14 wherein the liquid phase mixture is essentially anhydrous.

16. The process of claim 14 wherein the amount of water in the reaction is less than about 25 weight % of the weight of the mixture.

17. The process of claim 16 wherein the amount of water in the reaction is less than about 15 weight % of the weight of the mixture.

18. The process of claim 15 wherein the amount of water in the reaction is less than about 10 weight % of the weight of the mixture.

19. The process of claim 1 wherein the Bronsted acid is a nitrogen containing compound.

20. The process of claim 19 wherein the nitrogen containing compound is an amino containing compound.

21. The process of claim 1 wherein the process is carried out in the presence of carbon monooxide.

22. The process of claim 2 wherein the process is carried out in the presence of carbon monooxide.

23. The process of claim 1 wherein the process is carried out at a temperature of from about 20° C. to about 300° C.

24. The process of claim 2 wherein the process is carried out at a temperature of from about 20° C. to about 300° C.

25. The process of claim 23 wherein the process is carried out at a temperature of about 50° C. to about 200° C.

26. The process of claim 24 wherein the process is carried out at a temperature of about 50° C. to about 200° C.

27. The process of claim 1 wherein the pressure of the reaction is subatmospheric, atmospheric or superatmospheric.

28. The process of claim 2 wherein the pressure of the reaction is subatmospheric, atmospheric or superatmospheric.

29. The process of claim 27 wherein the reaction pressure is from about $10^{-6}$ torr to about 5,000 psia.

30. The process of claim 28 wherein the reaction pressure is from about $10^{-6}$ torr to about 5,000 psia.

31. The process of claim 29 wherein the reaction pressure is from about $10^{-5}$ torr to about 800 psia.

32. The process of claim 30 wherein the reaction pressure is from about $10^{-5}$ torr to about 800 psia.

33. The process of claim 31 wherein the reaction pressure is from about $10^{-4}$ torr to about 550 psia.

34. The process of claim 32 wherein the reaction pressure is from about $10^{-4}$ torr to about 550 psia.

35. The process of claim 1 wherein the mole ratio of the Bronsted acid to ruthenium is at least 0.5/1.

36. The process of claim 2 wherein the mole ratio of the Bronsted acid to ruthenium is at least 0.5/1.

37. The process of claim 35 wherein the mole ratio of the Bronsted acid to ruthenium is about 50/1 to about 1,000,000/1.

38. The process of claim 36 wherein the mole ratio of the Bronsted acid to ruthenium is about 50/1 to about 1,000,000/1.

39. The process of claim 1 wherein the ruthenium catalyst concentration is from about 30,000 parts to about 0.5 part per million ruthenium based on the weight of the liquid phase reaction mixture.

40. The process of claim 27 wherein there is present a solvent non-reactant for at least one of the reactants.

41. The process of claim 28 wherein there is present a solvent non-reactant for at least of the reactants.

42. The reaction of claim 29 wherein the pressure ranges from about 16 to about 5,000 pounds per square inch absolute.

43. The reaction of claim 30 wherein the pressure ranges from about 16 to about 5,000 pounds per square inch absolute.

44. The process of claim 27 wherein the pressure is subatmospheric.

45. The process of claim 28 wherein the pressure is subatmospheric.

46. The process of claim 4 wherein the product of transvinylation is divinyl adipate.

47. The process of claim 4 wherein the product of transvinylation is divinyl isophthtalate.

48. The process of claim 4 wherein the product of transvinylation is divinyl terephthtalate.

49. The process of claim 4 wherein the product of transvinylation is vinyl propionate.

50. The process of claim 4 wherein the product of transvinylation is vinyl stearate.

51. The process of claim 4 wherein the product of transvinylation is vinyl salicylate.
52. The process of claim 4 wherein the product of transvinylation is vinyl cinnamate.
53. The process of claim 4 wherein the product of transvinylation is vinyl 2-ethylhexanoate.
54. The process of claim 4 wherein the product of transvinylation is vinyl cyclohexanoate.
55. The process of claim 4 wherein the product of transvinylation is N-vinyl pyrrolidinone.
56. The process of claim 4 wherein the product of transvinylation is N-vinyl succinimide.
57. The process of claim 4 wherein the product of transvinylation is vinyl phenyl ether.
58. The process of claim 4 wherein the product of transvinylation is N-vinyl 2-oxazolidinone.
59. The process of claim 4 wherein the product of transvinylation is N-vinyl ethyleneurea.
60. The process of claim 4 wherein the product of transvinylation is 2-vinyloxyethyl acetate.
61. The process of claim 4 wherein the product of transvinylation is 2-vinyloxyethyl acrylate.
62. The process of claim 4 wherein the product of transvinylation is 2-vinyloxyethyl methacrylate.
63. The process of claim 4 wherein the product of transvinylation is 2-vinyloxyethyl pivalate.
64. The process of claim 4 wherein the product of transvinylation is vinyl palmitate.
65. The process of claim 4 wherein the product of transvinylation is 2-hydroxyethyl 5-vinyl ethylene-urea.
66. The process of claim 4 wherein the product of transvinylation is 1-(2-acetoxyethyl)-2-vinyloxy-imidazoline.
67. The process of claim 4 wherein the product of transvinylation is 2-acetoxyethyl-5-vinyl ethylene urea.
68. The process of claim 4 wherein the product of transvinylation is vinyl (1,1,1,3,3,3-hexafluoro-2-propyl) ether.
69. The process of claim 4 wherein the product of transvinylation is vinyl (2,2-di-phenyl acetate)
70. The process of claim 4 wherein the product of transvinylation is vinyl 2-benzoyl benzoate
71. The process of claim 4 wherein the product of transvinylation is vinyl neo-heptanoate.
72. The process of claim 4 wherein the product of transvinylation is vinyl neo-nonanoate.
73. The process of claim 4 wherein the product of transvinylation is hexyl vinyl ether.
74. The process of claim 4 wherein the product of transvinylation is vinyl (N-acetylamino-caproate).
75. The process of claim 4 wherein the product of transvinylation is vinyl (n-pivoylamino-caproate)
76. The process of claim 4 wherein the product of transvinylation is vinyloxy (tri-n-propyl) silane.
77. The process of claim 4 wherein the product of transvinylation is 5-isobenzofuran-carboxylic acid, 1,3-dihydro-1,3-dioxo-ethenyl ester.
78. The process of claim 4 wherein the product of transvinylation is N-vinyl o-toluene sulfonamide.

* * * * *

UNITED STATES PATENT AND TRADEMARK OFFICE
CERTIFICATE OF CORRECTION

PATENT NO. : 4,981,973
DATED : January 1, 1991
INVENTOR(S) : Rex E. Murray

It is certified that error appears in the above-identified patent and that said Letters Patent is hereby corrected as shown below:

Column 12, line 30, "ethyl ethyl" should read --ethyl ethylene- --.

Column 12, line 31, "eneurea" should read --urea--.

Column 12, line 32, "ethyl" should read --ethylene- --.

Column 12, line 33, "eneurea" should read --urea--.

Column 16, line 48 (Claim 41, line 2), --one-- should be inserted after "least".

Signed and Sealed this

Ninth Day of February, 1993

Attest:

STEPHEN G. KUNIN

Attesting Officer

Acting Commissioner of Patents and Trademarks